United States Patent [19]

Norris et al.

[11] 4,369,778

[45] Jan. 25, 1983

[54] METHOD AND APPARATUS FOR A PORTABLE RESPIRATOR

[76] Inventors: Amos Norris, Box 638; Edwin J. Dorius, 103 W. Juniper La., both of Gillette, Wyo. 82716

[21] Appl. No.: 252,234

[22] Filed: Apr. 8, 1981

[51] Int. Cl.³ ............................................. A61M 16/00
[52] U.S. Cl. .................................. 128/205.13; 128/28
[58] Field of Search ...................... 128/205.13, 205.17, 128/202.28, 202.29, 300, 282, 910, 28

[56] References Cited

U.S. PATENT DOCUMENTS

| | | | |
|---|---|---|---|
| 3,683,922 | 8/1972 | Cutter | 128/300 |
| 4,109,651 | 8/1978 | Steigerwald | 128/910 |

FOREIGN PATENT DOCUMENTS

| | | | |
|---|---|---|---|
| 1935371 | 10/1970 | Fed. Rep. of Germany | 128/205.17 |
| 2213764 | 9/1973 | Fed. Rep. of Germany | 128/205.17 |
| 2446115 | 9/1980 | France | 128/205.13 |

*Primary Examiner*—Henry J. Recla
*Attorney, Agent, or Firm*—Victor J. Evans & Co.

[57] ABSTRACT

Disclosed herein is a portable respirator and method of using same which includes a container having an enlarged opening that is flared outwardly, adapted to fit over the mouth area of a person requiring resuscitation, a plurality of unrestricted fenestrations closely placed together and disposed at an end of the container remote from the enlarged opening, in which the fenestrations are grouped in such a manner that a palm area of a rescuer's hand can cover all fenestrations and thereafter applying the same hand's fingers along a resilient deformable body portion from the opening to the fenestrations so that when the palm area occludes the fenestrations. Deforming the body portion will provide an air pulse into the mouth of a person to be rescued. Optimally, the person to be rescued nostrils are closed with the other hand so that the air pulse will have maximum impact.

6 Claims, 2 Drawing Figures

METHOD AND APPARATUS FOR A PORTABLE RESPIRATOR

BACKGROUND OF THE INVENTION

The prior art is rich in devices to assist in giving artificial respiration.

The ensuing list of references each teach the use of a device for providing artificial respiration:

| | |
|---|---|
| 2,428,451 Emerson | 3,216,413 Mota |
| 3,009,459 Ruben | 3,363,833 Laerdal |
| 3,136,312 Gattone | |

Of these Ruben teaches the use of an apparatus in which a central bulbous bag has at opposed extremities a face mask and a check valve so that depressing the bag will provide incremental air pulses through each of the check valves.

Similarly Laerdal teaches the use of an elastic bag for artificial respiration in which a check valve 13 is disposed at one extremity, to allow air to be introduced through a mask by means of collapsing a bellows type of container.

Likewise, the patent to Gattone requires the use of plural check valves in combination with a mask in which an air canister is provided for the introduction of gas into the person.

Mota teaches the use of a portable artificial respirator of the bellows type, in which inlet and outlet valves are provided to provide selective migration of air to the person being rescued, and a face engaging area completely surrounding the nose and lip area so that air can be continuously pumped into the person to be saved.

Clearly, all of these devices are rendered inoperable should any of those valves mentioned above fail to operate. Moreover, there is a certain likelihood that the detection of a valve having failed will go unnoticed during the excitement that normally exists in a crisis situation.

By way of contrast, the instant invention is directed to and claims a method and apparatus for providing artificial respiration in which the device is suitably dimensioned to be accommodated in the palm of most people in such a manner that fenestrations at one end of the container can be occluded by the palm, the container is suitably dimensioned to allow finger areas to grasp the central body area of the device so that depression of the container will provide an air pulse and its associated life saving benefits to the user. Simultaneously, the other hand is left available to close the nostrils of the person needing rescue. The container is provided with a central thicken area to allow a greater surface area to be depressed when manipulated by the fingers so that a large air pulse can be injected into the patient. The container is formed of a suitable plastic having a memory so that after deformation and releasing by the fingers, the container will return to its unstressed state.

SUMMARY AND OBJECTS OF THE INVENTION

Accordingly, this invention has as an object to provide an artificial respiration device which is foolproof in construction, and very simple to use.

It is yet a further object of the invention to provide a device of the character described above in which there are no parts associated therewith to malfunction.

It is still another object of this invention to provide a device of the character described above which lends itself to mass production techniques and is so reasonable in cost that every household can afford to have one.

It is still another object of this invention to provide a device of the character described above which is extremely easy to manipulate even for people of all ages, so that the benefits associated with artificial respiration will not be lost by any.

These and other objects will be manifest when considering the following detailed specification when taken in conjunction with the appended drawing figures.

DESCRIPTION OF THE DRAWINGS FIGURES

FIG. 1 is a side view with partial section fragmented showing the apparatus according to the present invention; and FIG. 2 is a sectional view taken along 2—2 of FIG. 1.

DESCRIPTION OF THE PREFERRED EMBODIMENT

Figure 1:
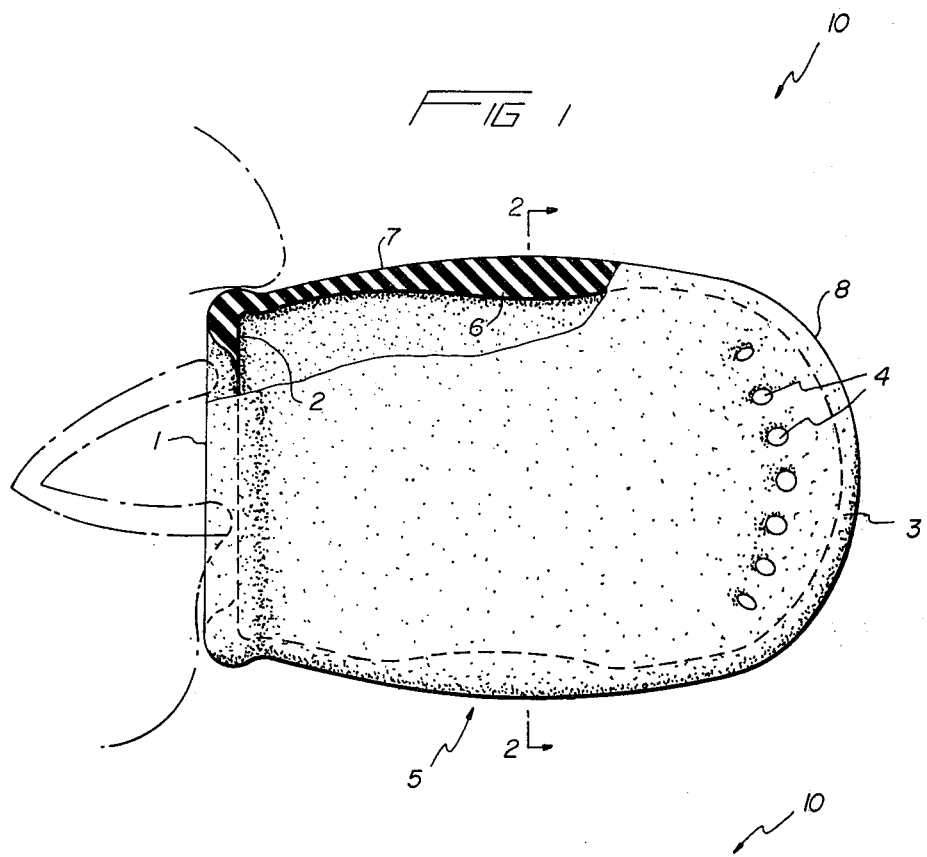

Referring to the drawings now wherein like reference numerals refer to like parts throughout the various drawing figures, reference numeral 10 is directed to the container according to the present invention.

The container 10 is provided with an enlarged opening 1 having an outwardly flared lip area or skirt 2 adapted to engage the periphery of a person's mouth in good sealing engagement without doing damage thereto, so that when thusly disposed over the person's mouth, a seal is effected and air pumped into the person's mouth will not leak around the periphery.

Figure 2:
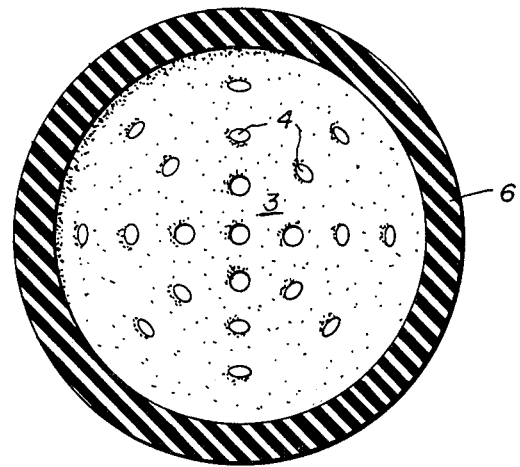

The end of the container remote from the opening 1 is provided with an arcuate surface 8 and the end 3 has a plurality of fenestrations 4 disposed in a matrix or array as best seen in FIG. 2 such that the palm area of most person's hand can easily occlude all of the fenestrations.

The central body area 5 of the container is provide with a thickened portion 6 in substantially an annular band construction as shown in FIG. 1, so that when fingers of the user grasp the thickened area, deformation of the container will occur over a larger area thereby pulsing a greater amount of air into the person's mouth. As shown by the drawings, the thickened area 6 gradually tapers thereafter to thinned portion 7 so that the amount of pressure required by the fingers is not excessive.

In use and operation, the enlarged opening is placed over the mouth of the person, the nostrils of the person are closed or shut by the hand of the person rescuing, and the end 3 is grasped within the palm area. The fenestrations have been occluded, and the fingers of that hand depress the container inwardly providing an air pulse into the person's mouth after which removal of the palm will allow air to reenter into the container allowing the container to expand back to its orginal shape. It is to be noted that the container is formed of a resilient deformable container having a memory whereby the container will return to its orginal unstressed state.

Moreover, having thus described the invention, it should be apparent that numerous structural modification are contemplated as being part of this invention as set forth hereinabove and defined hereinbelow by the claims.

What is claimed is:

1. A portable respirator comprising in combination:
   a container having an enlarged opening adapted to fit over the mouth area of a person requiring resuscitation,
   a plurality of unrestricted fenestrations closely placed together and disposed on an end of said container remote from said enlarged opening,
   said fenestrations grouped in such a manner that the palm area of a rescuer's hand can cover all fenestrations,
   and a resilient deformable body portion extending from said end to said opening whereby when said fenestrations are closed by occlusion with the palm, the fingers can deform said body portion to provide an air pulse to the person.

2. The device of claim 1 wherein said opening has an outwardly flared lip to assure comfortable but sealing engagement with the mouth area of the person.

3. The device of claim 2 wherein said body portion has a central annular thickened area to allow greater support in providing a greater air pulse when grasped by the fingers by providing greater deformation.

4. The device of claim 3 wherein said container is formed from a plastic having a memory to return the container to an origional, unstressed shape.

5. A method of providing resuscitation comprising providing a container with an enlarged opening at one end, a plurality of closely grouped fenestrations at a remote end, and a resilient deformable body portion extending from said one end to said remote end,
   placing said container's enlarged end over the mouth of the person,
   grasping said remote end,
   covering said fenestrations with the palm area of the hand, and depressing said resilient deformable body portion with fingers, while closing the nostrils of the person.

6. The method of claim 5 including releasing the nostrils and body portion of the container to allow a subsequent air pulse to be reproduced,
   and reintroducing more air into the person at a regular rate.

* * * * *